United States Patent [19]

Schouteten et al.

[11] 4,167,631

[45] Sep. 11, 1979

[54] PROCESS FOR THE PREPARATION OF CYANURIC ACID

[75] Inventors: Augustinus P. H. Schouteten, Maastricht; Marinus J.A.M. Den Otter, Munstergeleen, both of Netherlands

[73] Assignee: Stamicarbon, B.V., Geleen, Netherlands

[21] Appl. No.: 890,912

[22] Filed: Mar. 27, 1978

Related U.S. Application Data

[63] Continuation of Ser. No. 703,655, Jul. 8, 1976, abandoned.

[30] Foreign Application Priority Data

Jul. 8, 1975 [NL] Netherlands .......................... 7508098

[51] Int. Cl.$^2$ ......................................... C07D 251/32
[52] U.S. Cl. .................................................. 544/192
[58] Field of Search ........................................... 544/192

[56] References Cited

U.S. PATENT DOCUMENTS

| | | | |
|---|---|---|---|
| 3,563,987 | 2/1971 | Berkowitz | 544/192 |
| 3,635,968 | 1/1972 | Goelz et al. | 544/192 |
| 3,758,572 | 9/1973 | Jones et al. | 544/192 |
| 3,954,751 | 5/1976 | Fuchs et al. | 544/192 |

*Primary Examiner*—Dolph H. Torrence
*Attorney, Agent, or Firm*—Cushman, Darby & Cushman

[57] ABSTRACT

An improved process for the manufacture of cyanuric acid by heating a reaction solution of urea, biuret or mixtures thereof in a solvent and stripping the reaction solution with an inert auxiliary stripping gas. The inert auxiliary stripping gas is characterized as having a boiling point which ranges between that of ammonia and the reaction temperature at the reaction pressure.

10 Claims, 1 Drawing Figure

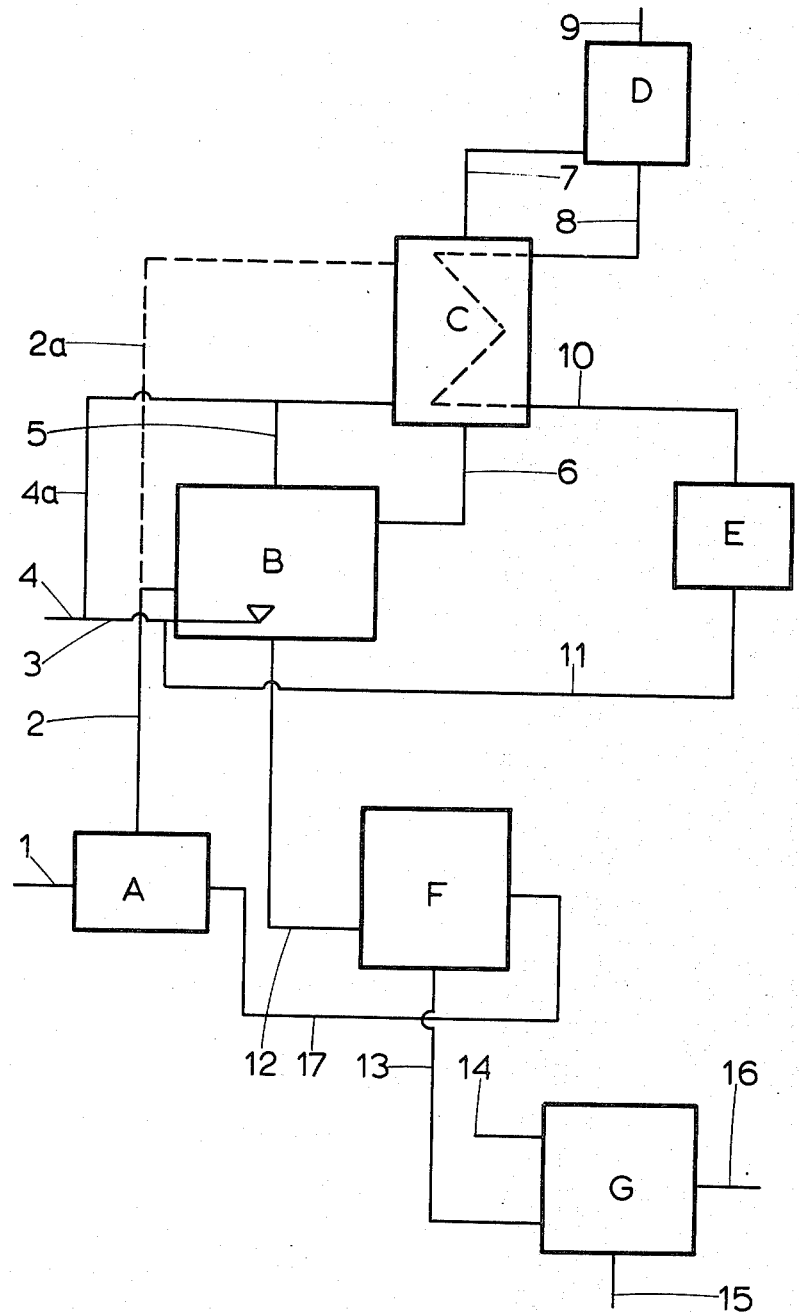

PROCESS FOR THE PREPARATION OF CYANURIC ACID

This is a continuation of application Ser. No. 703,655 filed July 8, 1976 and now abandoned.

BACKGROUND OF THE INVENTION

This invention relates to a process for the preparation of cyanuric acid by heating a reaction solution of urea, biuret or mixtures thereof dissolved in a solvent while stripping the reaction mixture with a stripping gas. Netherlands Patent Application 69.10466 and corresponding U.S. Pat. No. 3,635,968 describe such a process wherein N-cyclohexyl pyrrolidone is employed as a solvent and an inert gas such as nitrogen or carbon dioxide is passed through the reaction mixture to remove ammonia which forms during the reaction.

A problem which exists in such known processes resides in the fact that the valuable by-product ammonia must be recovered from a gaseous mixture which of course is highly diluted with the inert gas. Such recovery methods entail undesirably high costs. Such is also true with regard to recovery of gaseous solvent which may be contained in the vented waste gas from the reaction mixture.

Ammonia can, for example, be washed from the gaseous mixture with water, but this mode results in obtaining a dilute ammonia solution which normally would necessitate further concentration for use. Ammonia can also be recovered by condensation, but such methods are most expensive owing to the fact that at normal pressures, ammonia exists as liquid only at below $-30°$ C. Of course, one may raise the condensation temperature of ammonia by increasing the pressure, but such steps require considerable compression energy.

Consequently, none of these methods for recovering ammonia from the vent-gas mixture, which contains large amounts of inert gas, have proven satisfactory.

When the stripping treatment is omitted from such processes, one obtains an unsuitable product which is highly contaminated with aminated by-products such as ammelide and ammeline. It is important to obtain cyanuric acid having a low content of aminated by-products since generally an aminated by-product content of over one percent is commercially unacceptable. Therefore, crude cyanuric acid having an aminated by-product content in excess of one percent by weight is generally purified by treatment with an aqueous solution of a strong acid to hydrolyze ammelide and ammeline to cyanuric acid. However, such a hydrolysis step is expensive and thus it would be desirable to avoid same if possible.

Accordingly, it is the primary object of the present invention to provide a process for producing cyanuric acid whereby by-product ammonia may be readily separated from the vent gases resulting from the reaction mixture.

It is a further object of the present invention to provide a process for preparing cyanuric acid having a low aminated by-product content.

These and other objects of the present invention will be readily apparent from the description which follows.

DESCRIPTION OF THE INVENTION

Cyanuric acid is prepared according to the present invention by reacting a solution of urea, biuret or mixtures thereof in a solvent in a reaction zone at an elevated temperature while simultaneously stripping the reaction mixture with a stripping gas which is composed of vapor of an inert auxiliary stripping substance having a boiling point ranging between that of ammonia and the reaction temperature at the pressure under which the reaction is conducted.

According to the process of the present invention, by-product ammonia formed in the reaction is removed from the reactor as a gaseous mixture together with the vapor of the auxiliary stripping substance as well as some solvent vapor. A significant advantage of the present process resides in the fact that ammonia may easily and relatively inexpensively be recovered. Thus, in recovering ammonia according to the present invention, the gaseous mixture removed from the reactor is cooled to a temperature below the boiling point of the auxiliary stripping substance such that the auxiliary stripping substance condenses together with any solvent vapor that may be present. As a result, the only remaining component is gaseous ammonia which may then be discharged and recovered in a relatively pure state. Alternatively, one could readily condense the vapors of auxiliary stripping substance and solvent resulting from the vent-gas mixture, by means of compression or a combination of the lowering of gas temperature and elevation of pressure. As a result, without the expense of compression being involved, one may make use of the heat of condensation which results according to the present process, either elsewhere within the process or elsewhere.

In order to avoid unnecessary heat losses, it is preferred that one select an auxiliary stripping substance which has the lowest possible heat of evaporation and condensation. As noted above, the boiling point of the auxiliary stripping substance, at the reaction pressure must be less than the reaction temperature so as to insure an optimum stripping effect. Preferably, the boiling point of the auxiliary stripping substance is at least 30° less than the reaction temperature. Should the auxiliary stripping agent have a boiling point closer to the reaction temperature, the liquid phase in the reactor may contain a large amount of stripping agent which would result in complications when the reaction product is further processed. A preferred boiling point range of the auxiliary stripping agent is from about 25° to 180° C. When temperatures below 25° C. are employed, it is generally necessary that a cooling device be employed in the condensation. A particularly preferred boiling point range for the auxiliary stripping agent is from between about 80° to 160° C. Of course, the auxiliary stripping agent must be both inert and thermally stable under the reaction conditions.

Examples of suitable auxiliary stripping substances according to the process of the present invention include: aliphatic, aromatic, and mixed aliphatic-aromatic hydrocarbons having from three to twelve carbon atoms and preferably 6-9 carbon atoms per molecule. Also suitable are halogenated hydrocarbons having from one to ten carbon atoms and preferably from one to six carbon atoms per molecule. Also useful are mono- or poly- ethers, phenols, alkyl-substituted amides as well as tertiary amines. Examples include hexane, heptane, isooctane, cyclopentane, cyclohexane, methyl cyclohexane, benzene, toluene, xylenes, tetraline, tetrachloromethane, trichloroethene, chlorobenzene, diisoamyl ether, dioxane, the dimethyl ether of glycol ('dimethylcellosolve'), the dimethyl ether of diethylene glycol ('diglyme'), phenol, the cresols, N,N-dimethyl formamide, N,N-dimethyl acetamide, N,N,N,N,'-tetramethyl urea, and N,N-dimethyl aniline. If desired, a mixture of two or more auxiliary stripping substances may be used.

It is also possible to feed the auxiliary stripping substance as a liquid to the reactor, where it will evaporate and effect the stripping process. Preferably, the auxiliary stripping substance is fed to the reactor in the vapor phase.

It is also possible to recycle to the reactor part of the vent gas which escapes from the reactor and use the vent gas either alone or in combination with additional auxiliary stripping substance, as the stripping gas. The remainder of the vent gas is discharged. As a result, the vent gas will then contain relatively less auxiliary stripping substance and solvent vapor with respect to the ammonia, so that the ammonia can be recovered at lower cost. Also less auxiliary stripping substance and less solvent need be condensed and therefore results in a considerable cost saving in the recovery of both auxiliary stripping substance and the solvent. Moreoever, the heat contents of the recycled portion of the vent gas of the reactor are used again.

Still another advantage of the present process is the ease by which the supply of gas to the reactor may be increased, simply by raising the recycling ratio of the vent gas which requires only a small amount of energy. As a result, the stirring or agitation action of the recycle vent gas fed into the reactor can be increased with little expense.

The amount of auxiliary stripping substance employed is not critical, but should be sufficient to remove the ammonia formed in the reaction. Under these circumstances, a mechanically-unstirred round gas reactor may be used and the superficial gas velocity at which stripping gas is fed to the reactor may suitably range from about 0.1 to 1.0 and preferably 0.3 to 0.5 m/sec. The reaction mixture may be suitably stripped, for example, by bubbling the stripping gas through the mixture such that the mixture is contacted with the gas. Superficial gas velocity as used herein refers to superficial mass velocity as defined by Perry's Chemical Engineer's Handbook, Fourth Edition, pages 5-15, 1963, which is incorporated herein by reference.

In a preferred embodiment of the process according to the present invention, vent gas collected from the reaction zone is cooled in a first condenser to a temperature above the condensation temperature of the auxiliary stripping substance and the condensate is separated therefrom. The non-condensed vent gas remaining is then fed to a second condenser wherein the vapor of auxiliary stripping substance is condensed and separated out and ammonia is recovered in the gaseous phase from the second condenser. If desired, the auxiliary stripping substance condensate is then used as a cooling agent in the first condenser wherein a portion of the condensate may be evaporated. The condensate which is fed to the first condenser is then employed as the auxiliary stripping substance in the reaction zone by recycling to the reaction zone.

The solvent used in the present process must be such that urea, biuret and mixtures thereof are soluble therein but cyanuric acid is substantially insoluble. Furthermore, the solvent must be inert to the reactants and stable at the temperatures employed, thus having a high boiling point.

A wide variety of solvents are suitable for the process including for example dialkyl sulfones or cyclic sulfones having up to 12 carbon atoms, halogen-substituted cresols and phenols, N-alkyl pyrrolidones, N-substituted urethanes and cyclic urethanes having phenyl or alkyl group with up to six carbons as substituents, and cyclohexanol which if desired may be substituted with at least one hydrocarbon group having up to six carbon atoms. Suitable hydrocarbon groups include phenyl, alkyl or cycloalkyl groups. Thus, suitable solvents include dimethyl sulfone, dipropyl sulfone, sulfolane, chlorocresols, 5-methyl-2-oxazolidinone, diethylene glycol monomethyl ether, diethylene glycol diethyl ether, 2-methyl cyclohexanol, 2,6-dimethyl cyclohexanol and 2,4,6-trimethyl cyclohexanol. Preferred solvents include sulfolane and derivatives thereof having one or more methyl groups.

A catalyst which is soluble in the reaction mixture is preferably employed. The catalyst may be an acid, acid anhydride or ammonium salt of an acid. The catalyst is preferably organic and should not be very volatile under reaction conditions and thus should have a higher boiling point at reaction pressure than the temperature at which the reaction is carried out. Furthermore, the catalyst must have sufficient thermal stability under reaction conditions so as not to decompose. Suitable catalysts include such organic acids as both saturated and unsaturated high-boiling aliphatic carboxylic acids containing up to 24 carbon atoms, aromatic carboxylic acids, having up to 12 carbon atoms, both aliphatic and aromatic dicarboxylic acids having up to 12 carbon atoms and similar polycarboxylic acids, as well as the anhydrides and ammonium salts of the aforementioned acids.

As examples of suitable catalysts, to note but a few, include palmitic acid, oleic acid, stearic acid, benzoic acid, toluene carboxylic acids, naphthoic acids, phenyl acetic acid, succinic acid, phthalic acid, and 1,3,5-pentane tricarboxylic acid as well as the anhydride and ammonium salts of these acids. The acid, anhydride or ammonium salts may, if desired, contain substituents which are inert under reaction conditions such as alkyl groups from one to four carbon atoms, aryl groups having up to eight carbon atoms or halogen substituents. Preferred catalysts which are readily available include benzoic acid and ammonium benzoate.

The amount of catalyst which is added to the reaction mixture may vary greatly, but is noticeably effective at concentrations as low as 0.1% by weight of the total reaction mixture. While addition of more than 150 g/liter of catalyst is permissible such does not generally provide any advantage and thus the amount of catalyst added generally ranges from about 10 to about 150 gram per liter of the reaction mixture.

The reaction temperature may vary widely, and generally ranges from about 150 to about 280° C. Preferably the reaction is carried out at from about 170 to about 220° C. with an optimum being about 200° C. when sulfolane or a derivative thereof is the solvent. While the reaction may proceed more rapidly at higher temperatures, there is a greater chance of forming additional ammelide by-product and decomposing the solvent.

The reaction pressure is not critical and may also vary widely, ranging for example from about 0.1 to 10 atmospheres. Suitably the reaction may be carried out at about atmospheric pressure, for example between about 0.5 and 2 atmospheres. In some instances, it may be advantageous to carry the reaction out at below atmospheric pressure suitably in the range of from about 0.01 to 0.25 atmospheres.

In order to avoid undesirably high concentrations of ammelide in the cyanuric acid product, the concentration of the urea and/or biuret starting material should be kept low preferably at a level of 500 grams per kilogram of solvent or less. However, higher concentrations may be used but amounts in excess of the saturation level offer no advantage - preferably the concentration of urea, biuret or mixtures thereof ranges from about 100 to about 350 grams per Kg of solvent.

As noted above, a portion of the vent gas exiting the reactor may be recycled, preferably from about 60 to 99.9 percent by volume of the vent gas. The recycled vent gas is fed to the reactor so as to provide a degree of agitation in the reaction mixture which enhances the reaction. The stripping gas together with any additional stripping gas which may be used, is added to the reactor ssuitably at a rate sufficient to remove ammonia formed in the reaction. The total amount of gaseous stripping substance amounts suitably to from 50 to 1.000 liter per hour per liter of reaction mixture.

The process according to the present invention may be carried out suitably either batchwise or as a continuous process.

With reference to the accompanying drawing which schematically depicts a continuous process according to the present invention, urea, biuret or mixtures thereof is fed to a tank A through line 1 for dissolving in the solvent which in the present case is sulfolane.

The resulting solution flows through line 2 to reaction vessel B which is a gas-liquid-contactor wherein the conversion reaction to cyanuric acid is carried out. Through conduit 3, vapor of the auxiliary stripping substance, in this case xylene, is fed to reactor B. If desired, recycled vent gas which is removed from B through conduit 5 may be recycled through conduit 4a. A gaseous mixture (i.e. vent gas) consisting of xylene vapor, ammonia and sulfolane vapor passes through conduit 5 wherein a portion of the mixture may be recycled to the reaction vessel B through conduits 4a and 3 while the non-recycled vent gas is fed to a first condenser C. In condenser C, the vent gas is cooled to a temperature above the condensation temperature of the auxiliary stripping substance so as to condense solvent vapor. Both the auxiliary stripping substance and ammonia remain in the vapor state in condenser C while the resulting liquid phase is returned to the reactor B through conduit 6. Suitably, condenser C may be a scrubber, wherein the scrubbing liquid is preferably a solution of urea, biuret or mixtures thereof in the solvent employed which is fed to condenser C via conduit 2a.

The remaining gaseous mixture which is not condensed in C is then passed through conduit 7 to a second condenser D wherein the vent gas is further cooled and the auxiliary stripping substance is condensed. As a result, essentially pure ammonia in the gaseous phase is recovered through conduit 9. The condensate of auxiliary stripping substance is removed from condenser D by way of conduit 8 and serves as a cooling agent to the first condenser C wherein it evaporates eitherwholly or in part. The condensate is then passed through conduit 10 and if desired, passed through an evaporator E and then recycled to the reactor B via conduits 11 and 3 where it serves as a stripping gas.

From reactor B a suspension of cyanuric acid in the solvent flows through conduit 12 to separator F wherein the cyanuric acid is separated by means of filtration, precipitation, decantation, centrifuging or other conventional means from the solvent. The remaining solid product is passed by means of conveyor 13 to washing device G wherein the cyanuric acid product is washed with a suitable washing liquid which is supplied by conduit 14. The washing liquid employed in this instance is water which is removed from washing device G by means of conduit 15. The pure cyanuric acid is discharged through conduit 16. If desired, the cyanuric-acid product conveyed from separator F through conduit 13 may be subjected to an acid hydrolysis treatment with a strong mineral acid such as nitric acid or sulphuric acid according to conventional methods so as to hydrolyze the by-product ammelide and ameline to cyanuric acid. However, such a hydrolysis treatment is generally not necessary since the ammelide content of the cyanuric acid produced is sufficiently low for most applications. As the mother liquor which is separated off from the solid product in the separator F will often contain unconverted urea, biuret or mixtures thereof, it is separated and returned to the dissolving vessel A through conduit 17.

In a continuous operation according to the present invention, at the outset a given amount of solvent and catalyst, if present, are placed in reactor B. Solvent and catalyst are recycled throughout the process with any losses being replenished through conduits (not shown) located somewhere in the system, preferably the reactor.

The auxiliary stripping substance is initially added at 4 in a continuous operation. The reaction commences upon heating the contents of the reactor after which ammonia is formed from the reaction mixture. It is also possible to introduce the auxiliary stripping substance in liquid form to reactor B at the start of a continuous process. After the reactor contents have been heated, the circulation of the auxiliary substance is established and the feed of auxiliary stripping substance vapor through conduit 4 may be reduced or discontinued.

The following examples are offered in order to more fully illustrate the invention but are not to be construed as limiting the scope thereof.

EXAMPLES I-VI

In each of the examples as set forth in the table hereinbelow, 1 Kg of sulfolane having 70 grams of benzoic acid dissolved therein as a catalyst, is heated to about 160° C. with stirring. Thereafter, 275 grams of urea are fed to the reactor and the reactor is heated further to 190° C. After reaching the reaction temperature of 190° C., 13.4 g moles of auxiliary stripping substance per hour are fed into the liquid through a heated conduit. The pressure in the reactor is maintained at 1 atmosphere.

After the reactor has been maintained at a reaction temperature of 190° C. for 1 hour, the feed of the auxiliary stripping substance is discontinued and the reaction mixture filtered off at once. Upon cooling the filter cake to 30° C., it is washed with toluene, dried and analyzed. The results of the analysis are set forth in the table hereinbelow. In each case, the ammeline content of the solid substance was 0.01% by weight or less.

TABLE

| Example | Auxiliary Stripping Substance | Composition of solid substance, % by weight | |
|---|---|---|---|
| | | cyanuric acid | ammelide |
| I | xylene | 97.0 | 0.2 |
| II | cyclohexane | 95.4 | 0.2 |
| III | n-heptane | 91.8 | 0.3 |
| IV | monochlorobenzene | 98.7 | 0.3 |
| V | dioxane | 97.2 | 0.3 |
| VI | 'diglyme' | 95.2 | 0.2 |

The invention, in its broadest aspects, is not limited to the specific details shown and described, but departures may be made from such details within the scope of the accompanying claims, without departing from the principles of the invention.

Furthermore, the invention claimed herein may compromise, consist of or consist essentially of the hereinabove recited steps and materials.

We claim:

1. In a process for the preparation of cyanuric acid by heating a reaction solution of urea, biuret or mixtures thereof in a solvent and stripping the solution with a stripping gas to remove ammonia therefrom, the improvement which comprises stripping the reaction solution with an inert auxiliary stripping substance having a boiling point ranging between that of ammonia and the reaction temperature and being from about 25° to 180° C. at the reaction pressure.

2. A process according to claim 1 above wherein said inert auxiliary stripping substance has a boiling point between about 80° and 160° C.

3. A process according to claim 1 wherein said auxiliary stripping substance is an aliphatic, aromatic or mixed aliphatic-aromatic hydrocarbon having from 3 to 12 carbon atoms.

4. A process according to claim 3 wherein the hydrocarbon has from 6 to 9 carbon atoms.

5. A process according to claim 1 wherein said auxiliary stripping substance is a halogenated hydrocarbon containing from 1 to 10 carbon atoms.

6. A process according to claim 5 wherein said halogenated hydrocarbon contains from 1 to 6 carbon atoms.

7. A process according to claim 1 wherein the inert auxiliary stripping substance is a mono- or poly- ether.

8. A process according to claim 1 which further comprises:
    (a) cooling vent gas which escapes the reaction zone in a first condenser to a temperature above the condensation temperature of the inert auxiliary stripping substance,
    (b) separating the condensate from non-condensed gas,
    (c) feeding the non-condensed gas to a second condenser,
    (d) condensing and separating the inert auxiliary stripping substance from gaseous ammonia, and
    (e) recovering gaseous ammonia from the second condenser.

9. A process according to claim 8 wherein the inert auxiliary stripping substance which is condensed in said second condenser is first used as a cooling agent in said first condenser whereby at least a portion is evaporated and then is recycled to the reaction zone as an auxiliary stripping substance.

10. A process according to claim 1 wherein the concentration of urea, biuret or mixtures thereof is at a level of 500 grams or less per kilogram of solvent.

* * * * *